US008987163B2

(12) United States Patent
Galvis et al.

(10) Patent No.: US 8,987,163 B2
(45) Date of Patent: Mar. 24, 2015

(54) PRODUCTION OF LOWER OLEFINS FROM SYNTHESIS GAS

(71) Applicant: Nederlandse organisatie voor wetenschappelijk onderzoek (NWO), The Hague (NL)

(72) Inventors: Hirsa Maria Torres Galvis, Utrecht (NL); Johannes Hendrik Bitter, Odijk (NL); Krijn Pieter de Jong, Houten (NL)

(73) Assignee: Nederlandse organisatie voor wetenschappelijk onderzoek (NWO), The Hague (NL)

( * ) Notice: Subject to any disclaimer, the term of this patent is extended or adjusted under 35 U.S.C. 154(b) by 0 days.

(21) Appl. No.: 14/205,969

(22) Filed: Mar. 12, 2014

(65) Prior Publication Data
US 2014/0256542 A1    Sep. 11, 2014

Related U.S. Application Data

(62) Division of application No. 13/503,481, filed as application No. PCT/NL2010/050711 on Oct. 25, 2010, now Pat. No. 8,703,830.

(30) Foreign Application Priority Data

Oct. 23, 2009  (EP) ..................................... 09173928

(51) Int. Cl.
*B01J 31/00* (2006.01)
*B01J 27/128* (2006.01)
*B01J 23/745* (2006.01)
*B01J 21/04* (2006.01)
*B01J 21/18* (2006.01)
*B01J 23/889* (2006.01)
*B01J 27/224* (2006.01)
*B01J 35/10* (2006.01)
*B01J 37/02* (2006.01)
*B01J 37/03* (2006.01)
*B82Y 30/00* (2011.01)
*C07C 1/04* (2006.01)

(52) U.S. Cl.
CPC ............... *B01J 23/745* (2013.01); *B01J 21/04* (2013.01); *B01J 21/185* (2013.01); *B01J 23/8892* (2013.01); *B01J 27/224* (2013.01); *B01J 35/1014* (2013.01); *B01J 35/1019* (2013.01); *B01J 35/1038* (2013.01); *B01J 35/1042* (2013.01); *B01J 37/0201* (2013.01); *B01J 37/0203* (2013.01); *B01J 37/0211* (2013.01); *B01J 37/035* (2013.01); *B82Y 30/00* (2013.01); *C07C 1/044* (2013.01); *C07C 1/0445* (2013.01); *C07C 2521/04* (2013.01); *C07C 2521/18* (2013.01); *C07C 2523/745* (2013.01); *C10G 2400/20* (2013.01); *C10G 2300/1022* (2013.01); *C10G 2300/4006* (2013.01)

USPC ........................... 502/107; 502/154; 502/229

(58) Field of Classification Search
USPC .......................................... 502/107, 154, 229
See application file for complete search history.

(56) References Cited

U.S. PATENT DOCUMENTS

2004/0077737 A1    4/2004   Eri et al.

FOREIGN PATENT DOCUMENTS

| DE | 2822656 | 12/1978 |
| WO | WO84/00702 | 3/1984 |
| WO | WO97/32813 | 9/1997 |

OTHER PUBLICATIONS

Peigney et al., Carbon nanotubes Fe-alumina nanocomposite,(Journal of the European Ceramic Society (1998),18(14), 1995-2004).*
Chinese Abstract CN 101396662, 2009.*
Barkhuizen, D. et al., "Experimental approaches to the preparation of supported metal nanoparticles", Pure Appl. Chern., vol. 78, No. 9, 2006, pp. 1759-1769, XP002578988.
Barrault, J. et al., "Selective Hydrocondensation of CO to Light Olefins With Alumina~Upported Iron Catalysts", React. Kinet. Catal. Lett., vol. 15, No. 2, 153-158, 1980, XP002578990.
Galvis et al., "Supported Iron Nanoparticles as Catalysts for Sustainable Production of Lower Olefins", Science 335:835-838, 2012.
Koeken et al., "Suppress of Carbon Deposition in the Iron-Catalyzed Production of Lower Olefins from Synthesis Gas", Angew. Chem. Int. Ed. 51:1-5, 2012.
PCT/NL2010/050711 International Preliminary Report on Patentability, 16 pages, Feb. 14, 2012.
PCT/NL2010/050711 International Search Report and Written Opinion, 10 pages, Feb. 11, 2011.
Zhang et al., "Method for preparing nanosized catalyst for producing low carbon alkene from synthesis gas," Chinese Abstract CN 101396662 (Apr. 2009).

* cited by examiner

Primary Examiner — Jafar Parsa
(74) Attorney, Agent, or Firm — Fish & Richardson P.C.

(57) ABSTRACT

Disclosed is a process for the production of lower olefins by the conversion of a feed stream comprising carbon monoxide and hydrogen, and catalysts as used therein, such as a Fischer-Tropsch process. By virtue of the invention, lower olefins can be formed from synthesis gas, with high selectivity, and low production of methane. The catalysts used herein comprise an α-alumina support, and a catalytically active component that comprises iron-containing particles dispersed onto the support in at least 1 wt. %. The majority of the iron-containing particles is in direct contact with the α-alumina and is well-distributed thereon. Preferably, the iron-containing particles have an average particle size below 30 nm, and most preferably below 10 nm. The supported catalysts not only show a high selectivity, but also a high catalyst activity and chemical and mechanical stability.

6 Claims, 3 Drawing Sheets

PRODUCTION OF LOWER OLEFINS FROM SYNTHESIS GAS

CROSS-REFERENCE TO RELATED APPLICATIONS

This application is a divisional of U.S. patent application Ser. No. 13/503,481, filed Apr. 23, 2012, which is a U.S. National Phase Application of International Patent Application No. PCT/NL2010/050711 filed Oct. 25, 2010, and entitled "Production of Lower Olefins from Synthesis Gas," which claims priority to European Patent Application Ser. No. 09173928.4 filed on Oct. 23, 2009," all of which are incorporated herein by reference.

FIELD OF THE INVENTION

The invention pertains to the production of lower olefins from a feed stream comprising carbon monoxide and hydrogen by means of, e.g., a Fischer-Tropsch process, using a supported iron-based catalyst. Particularly, the invention pertains to the production of certain catalysts for use therein.

BACKGROUND OF THE INVENTION

The invention generally applies to the conversion of synthesis gas. Synthesis gas (or "syngas") in the context of the invention refers to a mixture comprising carbon monoxide and hydrogen. Synthesis gas generally also comprises $CO_2$. For use in the production of olefins by means of a Fischer-Tropsch process, the $CO_2$ is preferably removed, reduced, or otherwise adjusted so as to provide the desired $H_2$ : CO ratios discussed below.

Synthesis gas is generally produced by methods such as steam reforming of natural gas or heavier hydrocarbons to produce hydrogen, or the gasification of coal, of biomass, and in some types of waste-to-energy gasification facilities. Particularly with reference to its potential biomass and waste origin, synthesis gas is increasingly receiving attention as an environmentally friendly, sustainable, resource of carbon-based chemicals.

Useful applications of synthesis gas will generally require chemical conversion of the gaseous CO and $H_2$ components into hydrocarbons such as fuels or monomers, e.g. by Fischer-Tropsch synthesis.

The Fischer-Tropsch process is a catalyzed chemical reaction in which synthesis gas is converted into a range of hydrocarbons of various forms. The most common catalysts are based on iron and cobalt, although nickel and ruthenium have also been used. The principal purpose of this process is to produce a synthetic petroleum substitute, typically from coal, natural gas or biomass, for use as synthetic lubrication oil or as synthetic fuel.

The Fischer-Tropsch process involves a variety of competing chemical reactions, which lead to a series of desirable products and undesirable byproducts. When using cobalt catalysts, the most important reactions are those resulting in the formation of alkanes. These can be described by chemical equations of the form:

$$(2n+1)H_2 + nCO \rightarrow C_nH_{(2n+2)} + nH_2O$$

with 'n' being a positive integer. Since methane (n=1) is mostly considered an unwanted by-product, process conditions and catalyst composition are usually chosen to favor higher molecular weight products (n>1) and thus minimize methane formation. In addition to alkane formation, competing reactions result in the formation of alkenes, as well as alcohols and other oxygenated hydrocarbons. Usually, only relatively small quantities of these non-alkane products are formed, although iron-based catalysts favoring some of these products have been developed. The formation of alkenes generally is within the following limiting chemical equations (one being to the extreme of water formation, the other to the extreme of carbon dioxide formation):

$$2nH_2 + nCO \rightarrow C_nH_{2n} + nH_2O$$

or $$nH_2 + 2nCO \rightarrow C_nH_{2n} + nCO_2$$

Generally, the Fischer-Tropsch process is operated in the temperature range of 150-300° C. Higher temperatures lead to faster reactions and higher conversion rates, but also tend to favor methane production. As a result the temperature is usually maintained at the low to middle part of the range in the case of cobalt catalysts. Iron is usually employed at the higher end of the temperature range. Increasing the pressure favors the formation of long-chain alkanes, which is usually favorable for fuel production, but generally undesirable for the production of chemicals.

To the extent that Fischer-Tropsch processes have been described, this has very much focused on the production of fuels, i.e. selectivity towards an appropriate distribution of paraffins, e.g. with a view to providing desired fuel properties. This is quite a different field from the production of olefins, let alone lower olefins.

With the currently increasing attention for the use of sustainable resources of chemicals, and the use of biomass and waste streams, it is desired that synthesis gas can be put to use in a more versatile manner than the past focus on fuels. Thus it is desired to employ synthesis gas as a source of carbon also for chemicals.

Lower olefins are widely used in the chemical industry. They are mainly produced via naphtha and gas oil cracking, via paraffins dehydrogenation, or via FCC (fluid catalytic cracking). Environmental, economic and strategic considerations have encouraged the search of alternative feedstocks for the production of lower olefins. Different options have been considered such as natural gas, coal and biomass. In view hereof it is desired to provide a technically feasible and commercially attractive process to convert synthesis gas into lower olefins.

The invention preferably pertains to a specific Fischer-Tropsch process, viz. one that has been modified in order to yield lower olefins. Lower olefins, in the context of the invention, are straight-chain or branched alkenes having from 2 to 8, preferably from 2 to 6 carbon atoms, and most preferably this refers to $C_2$-$C_4$ alkenes. This process involves the use of supported iron-based catalysts, and reaction temperatures higher than 270° C., preferably higher than 300° C.

A supported catalyst is known to the person skilled in heterogeneous catalysis as a catalyst comprising a catalytically active part and a catalytically non-active part, wherein the catalytically non-active part (the support) generally forms the majority of the catalyst. This distinguishes a supported catalyst from a bulk-catalyst, in which the catalytically non-active part generally is the minority.

A reference to the selective hydrocondensation of carbon monoxide to light olefins, using alumina supported iron catalysts, is J. Barrault et al., React. Kinet. Catal. Lett., Vol. 15, No. 2, 153-158 (1980). This document indicates that, by changing the support, the catalyst activity can be enhanced, and light olefin selectivity can be increased. However, the results attained by Barrault are representative of a moderate light olefin selectivity only, and by far insufficient suppression of methane production. In fact, Barrault sets out a particular problem, in that the most active catalysts are also the least selective.

Another reference is WO 84/00702. Herein iron nitrate, together with a praseodymium promoter, is used on a modified (heat treated) γ-alumina support. The catalyst is employed in the Fischer-Tropsch process, wherein it is asserted that $C_{2-8}$ hydrocarbons are produced preferentially over methane. It is further indicated that a significant proportion of the hydrocarbons formed are 1-alkenes. The process is not, however, suited to selectively produce lower olefins over saturated hydrocarbons and, yet, keep methane production and higher olefins' production low. The heat-treated support has an α-alumina part and a γ-alumina part. The iron-containing particles are not detectably present on the α-alumina part.

Another reference that aims at producing lower olefins from synthesis gas, is DE 25 36 488 (1976). Herein an iron-based bulk catalyst is provided (iron with an oxide of titanium, zinc oxide and potassium oxide). Although, allegedly, this results in a process of high selectivity, with methane production only 10% and about 80% of lower olefins, the results therein are irreproducible and do not in fact lead to any suitable selectivity or reactivity.

Whilst all of the foregoing references represent unsuitable processes going back approximately 20-30 years in time, more recent development have not led to any success either, in terms of selective lower olefin production, effective suppression of methane production, and attractive catalyst activities or stabilities.

As to the latter, the chemical stability of the catalyst is an important issue in Fischer Tropsch processes. A chemically stable catalyst will be less prone to deactivation. In Fischer Tropsch processes, particularly with iron based catalysts and under conditions of temperature and pressure that favor alkene formation, catalyst deactivation is a serious problem. This is mainly due to coke formation, i.e. the undesired accumulation of carbon on the catalyst.

Thus, e.g., Sommen et al., Applied Catalysis 14 (277-288), 1985, describe Fischer-Tropsch catalysts that consist of iron oxide supported on activated carbon. Whilst these catalysts show an improved selectivity balance for lower olefins versus methane, the tested catalysts display a fast deactivation, i.e. they suffer from a low stability. Another drawback associated with activated carbon, is that it is prone to gasification, particularly at higher pressures and prolonged reaction times.

In WO 2009/013174 a promoted bulk iron catalyst is intended to be used in high temperature Fischer-Tropsch (340° C.) to produce lower olefins. Although methane selectivity of the claimed catalyst is low, the selectivity towards light olefins is insufficient. Moreover, the invention judiciously seeks to avoid bulk catalysts, and is specifically directed to supported catalysts.

Another issue with Fischer Tropsch catalyst performance is mechanical stability, e.g. vulnerability to fragmentation of catalyst particles related to extensive carbon laydown. This mechanical instability generally is an issue with bulk catalysts, particularly under conditions of increased catalyst activity, such as the elevated pressures typically used in industry. A reference in this regard is Shroff et al. Journal of Catalysis 156 (185-207), 1995. It is, inter alia, for this reason that the invention is specifically in the field of supported catalysts.

The present invention seeks to provide a Fischer-Tropsch route to lower olefins that has one or more of the following advantages:

a high selectivity for lower olefins, at cost of saturated hydrocarbons (paraffins), and higher olefins;
an effective suppression of the production of methane (i.e. a low selectivity for methane);
an increased catalytic activity, particularly without detracting from the results on selectivity.
a good chemical and mechanical stability, and particularly retaining this stability at elevated pressures as used in industry
a low amount of coke formation

SUMMARY OF THE INVENTION

In order to better address one or more of the foregoing desires, the invention, in one aspect, presents a process for the production of lower olefins by the conversion of a feed stream comprising carbon monoxide and hydrogen, preferably at a temperature above 270° C., and preferably not higher than 500° C., using a supported, iron-based catalyst, wherein a catalyst composition is provided that comprises iron-containing particles dispersed onto a support that comprises α-alumina (α-$Al_2O_3$), said support being loaded with at least 1 wt. % (calculated on the weight of the support) of the iron-containing particles, wherein the majority of the iron-containing particles is in direct contact with the α-alumina In another aspect the invention provides a process for the production of lower olefins by the conversion of a feed stream comprising carbon monoxide and hydrogen, preferably at a temperature above 270° C., and preferably not higher than 500° C., using a supported, iron-based catalyst, wherein a catalyst composition is provided that comprises iron-containing particles dispersed onto a support that comprises α-alumina (α-$Al_2O_3$), said support being loaded with at least 1 wt. % (calculated on the weight of the support) of the iron-containing particles, wherein the majority of the iron-containing particles has a particle size determined by Transmission Electron Microscopy of 30 nm or or lower.

In another aspect, the invention is the use of a catalyst composition as described above, to provide a catalyst in the selective Fischer-Tropsch production of lower olefins from synthesis gas.

In yet another aspect, the invention pertains to a process for the preparation of an iron-based catalyst composition comprising a support and an iron component, the process comprising the step of allowing an organic iron complex to decompose under the influence of heat, so as to form iron oxide nanoparticles, wherein the decomposition is conducted in the presence of the support material.

DETAILED DESCRIPTION OF THE INVENTION

In the iron-based catalysis of the Fischer-Tropsch process, the active phase of the iron catalysts is ultimately iron or iron carbide, formed in situ. The present invention is concerned with the catalyst composition as provided to the process. Whilst the iron-containing particles therein can be iron carbide itself, it is generally considered more convenient to provide the iron-containing particles in a different form, e.g. as iron oxide. The iron-containing particles in the catalysts as provided will hereinafter be indicated as "catalytically active" so as to distinguish this from the support.

Figure 5:
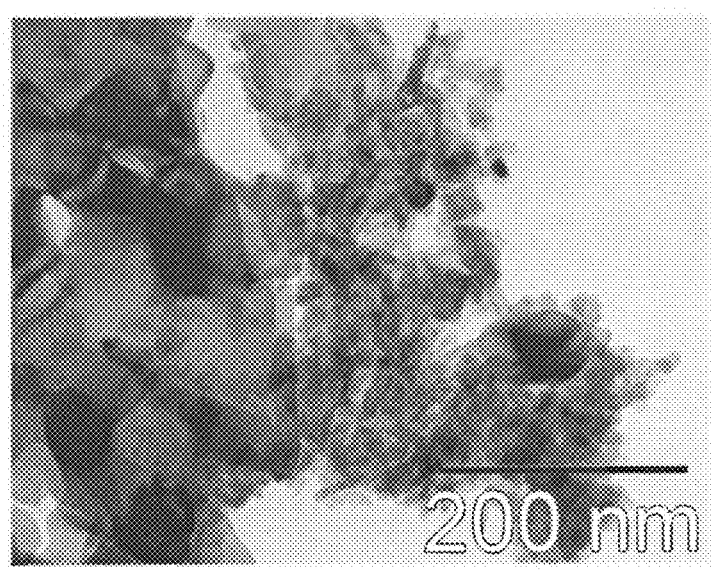
FIG. 5 is an electron micrograph of $Fe_2O_3$ supported on heat treated gamma alumina (not in accordance with the invention; Sample C-8).

The invention is based on providing a supported catalyst composition. Without wishing to be bound by theory, the inventors believe that an important factor in the favorable results attained with the catalysts used in the invention, is the judicious combination of a catalyst of the supported type (rather than a bulk catalyst), in conjunction with the requirement that a sufficient load of iron-containing particles is dispersed onto the α-alumina support, and that the majority of the iron-containing particles is in direct contact with the α-alumina None of the prior art documents teaches a catalyst that is of the supported type, that comprises an α-alumina support that is inert towards iron, and in which the support is loaded with iron-containing particles at a sufficiently high level, i.e. at least the minimum of 1 wt. % referred to above. E.g. in WO 84/00702 the iron appears to preferentially attach to the non-inert (γ-alumina) part of the catalyst, as can be derived from TEM analysis (FIG. 5).

Particularly, none of the prior art references achieves the combined results displayed by the invention, such as a low methane production (let alone as low as 11% selectivity), a high selectivity for lower olefins (let alone as high as 55%) and, moreover, does not achieve any such results in conjunction with an increased catalyst activity.

The iron-containing particles in the catalyst composition as provided, will preferably have a particle size of up to 50 nm. In a more preferred embodiment, the iron-containing particles are provided as relatively small active particles, having a particle size below 30 nm, more preferably below 20 nm, and most preferably below 10 nm.

In one aspect, the majority of the iron-containing particles has a particles size determined by Transmission Electron Microscopy of 30 nm or lower, and preferably 20 nm or lower. The requirements of particle size (which reflects that the catalytically active particles are well distributed over the support), and the required direct contact with the support, are interrelated. I.e., if particles are too large, they will be in a clustered form, only a small portion of which is in direct contact with the support. Preferably, both of these alternative ways of defining the catalyst, are together applicable to the majority (more than 50%, preferably more than 70%, more preferably more than 80%) of the numbr of the iron-containing particles.

In the art, it is generally taught that Fischer-Tropsch catalytic activity will drop when catalyst particles become too small. E.g., Barkhuizen et al., Pure Appl. Chem., Vol. 78, No. 9, pp 1759-1769, 2006, show that small crystallites with a size below 9 nm are much less active than larger crystallites. A similar teaching exists on cobalt particles, see Bezemer et al., J. Am. Chem. Soc. 2006, 128, 3956. In the present invention, the smaller particles (below 15 nm average particle size, and preferably below 10 nm), show increased selectivity, activity and stability.

Without wishing to be bound by theory, the present inventors believe that using the preferred smaller particles judiciously leads to providing voids between the active particles. These voids serve as a mechanical space, to prevent sintering and aggregation of catalyst active particles. Moreover, by the judicious choice for an α-alumina support, these voids are well-retained during use of the catalyst. In this respect it is further preferred that the particle size of the iron-containing particles is below 10 nm.

As indicated above, a supported catalyst will be understood as pertaining to a catalyst composition comprising a catalytically active part (i.e. particles as provided that are either active, or are converted into an active phase in situ), and a catalytically non-active part, wherein the catalytically non-active part (the support) generally forms the majority of the catalyst. This distinguishes a supported catalyst from a bulk-catalyst, in which the catalytically non-active part is generally the minority. Thus, in a supported catalyst, the catalytically non-active part is generally more than 50% by weight of the catalyst composition. Preferably the support forms more than 60% by weight and more preferably more than 80% by weight of the total catalyst composition.

The catalytically active part of the catalyst composition comprises iron-containing particles. The catalyst compositions provided in the present invention comprise these iron-containing particles dispersed onto the alpha-alumina support in an amount of at least 1 wt. % and generally up to 50 wt. %. Preferably the amount of iron-containing particles dispersed onto the alpha-alumina support is at least 10 wt. %.

The loading of the α-alumina support with a sufficient amount of iron-containing particles distinguishes the catalysts of the invention from catalysts, e.g., as described in the aforementioned WO 84/00702. The catalysts of the invention, as illustrated with reference to the examples and comparative examples below, show a clearly improved performance as compared to the catalyst of WO 84/00702. Thus, the selectivity for methane is reduced to less than half, and the selectivity for $C_2$-$C_4$ olefins is nearly doubled.

Without wishing to be bound by theory, the present inventors believe that in this catalyst, although an alpha-alumina like support material is present, the iron-containing particles will preferentially enter into chemical interaction with the also present non-inert, gamma-alumina support. In fact, hardly any iron-containing particles are present on the alpha-alumina part of the heat treated gamma-alumina support. In the present invention, iron-containing particles are present on, in or at the α-alumina support in the aforementioned amounts.

This presence is preferably associated with physical contact between the iron-containing particles and the α-alumina support. In the preferred catalyst compositions of the invention, iron-containing particles retained in physical contact with the α-alumina support are available to exert their catalytic activity.

In the present invention this is reflected in the requirement that the majority of the iron-containing particles (i.e. at least 50% of the number of particles) is in direct contact with the α-alumina support. This distinguishes the catalyst used in the invention from catalysts in which iron-containing particles are present in a substantially clustered form. In the latter case, only a minority of the iron-containing particles can be in direct contact with the support, as a substantial amount of the particles is present on top of, or otherwise adjacent to other iron-containing particles, thus lacking direct contact with the support.

Preferably, at least 50% of the iron-containing particles is in physical contact with the α-alumina support, more preferably at least 80% and most preferably at least 90%. This is particularly preferred in conjunction with the preferred lower particles sizes of the iron-containing particles. As a result, relatively small particles (particle size below 30 nm, preferably below 20 nm, and most preferably below 10 nm), in a sufficient load (generally 1-50 wt. % calculated on the weight of the support, preferably at least 10 wt. %), are present with a low extent of clustering, well dispersed onto the alpha-alumina support, and mostly standing alone (i.e. leaving voids in between).

Iron based catalysts can be synthesized using several iron containing precursors through different preparation methods. Examples of iron containing precursors are inorganic and organic iron salts, iron chelates, iron clusters, iron hydroxides and oxi-hydroxides, and iron organometallic complexes. Representative of these compounds are iron tetracarbonyl, iron pentacarbonyl, iron nonacarbonyl, iron nitrates, bromides, chlorides, fluorides, phosphates, sulfates, acetylacetonates, acetates, fumarates, gluconates, citrates, benzoates, maleates, oxalates, oleates, stearates, and the like. Iron precursors can provide iron in a ferrous form, a ferric form, or a combination thereof.

The catalyst precursors preferably comprise Fe(II) or Fe(III) in combination with organic ligands or anions such as acetate, citrate, EDTA (ethylene diamine tetra acetate) or NTA (nitrilo triacetate) and include in particular iron (II) carboxylate compounds, particularly hydroxy-carboxylic iron compounds which may be used as ammonium sodium or potassium salts, and ammonium iron citrate. The most preferred iron-containing particles are prepared from ammonium iron (III) citrate.

The above mentioned iron precursors are used to prepare iron containing particles which act as an active phase (generally after in situ conversion into iron carbide) in supported catalysts. Examples of catalysts preparation techniques are impregnation, deposition precipitation, ion exchange, electrochemical deposition, electrostatic adsorption, co-precipitation which are well-known techniques in the art (SYNTHESIS OF SOLID CATALYSTS. K. P. de Jong (Editor). Wiley-VCH Verlag GmbH & Co. Weinheim, 2009). The resulting iron-containing particles present in the catalyst composition as provided, preferably comprise an iron oxide, most preferable $Fe_2O_3$.

The iron-containing particles preferably have a judiciously low particle size. This refers to an average particle size of smaller than 30 nm. Preferably the particles are of smaller size, viz. having an average particle size below 20 nm. Most preferably, the average particle size is below 10 nm.

The average particle size of supported metal catalysts can be determined using different techniques. The preferred techniques to determine particle size are transmission electron microscopy (TEM), X-ray diffraction (XRD) line broadening and quantitative X-ray photoelectron spectroscopy (XPS). These techniques are well-known to the skilled person.

TEM is an analytical technique which allows the direct observation of the metal particles in a supported catalyst by means of an electron microscope in transmission mode. This technique is useful to determine the particle size distribution and the structural characteristics of the catalysts. Additional information about this method can be found in STRUCTURE OF METALLIC CATALYSTS. J. R. Anderson. Academic Press Inc. London, 1975. P. 363.

XRD: provided that crystallites smaller than 100 nm are present in the catalyst, appreciable line broadening in the x-ray diffraction pattern will occur. In the case where the material is stress free, the size is estimated from a single diffraction peak. The extent of the broadening is described as the full width at half maximum intensity of the peak and is used to calculate the mean crystallite diameter with the Scherrer equation, which is known to the skilled person. A reference on this technique is STRUCTURE OF METALLIC CATALYSTS. J. R. Anderson. Academic Press Inc. London, 1975. P. 365.

Quantitative XPS: The XPS peaks are dependent on the surface structure on the nanometer depth scale. The analysis of the peak shape of measured spectra provides information about the quantitative composition of the surface and the coverage surface fraction of the support. The data obtained from quantitative XPS analysis can be used with mathematical models to determine the distribution and phase thickness of surface species. An example of the use of quantitative XPS to determine average particle size is shown by Bezemer et al. in the characterization of cobalt catalysts (COBALT PARTICLE SIZE EFFECTS IN THE FISCHER-TROPSCH REACTION STUDIED WITH CARBON NANOFIBER SUPPORTED CATALYSTS. G. L. Bezemer et al. Journal of the American Chemistry Society 128 (2006): 3956-3964).

The catalyst, as is customary in the art, optionally comprises a promoter. In general a promoter is a substance that enhances the catalyst's performance in terms of any of selectivity, stability, activity, or combinations thereof. In literature basically all solid elements have been recognized as possible promoters, sometimes dependent on the concentration or other conditions of use. Preferred promoters comprise at least one element selected from the group consisting of calcium, cesium, chromium, cobalt, copper, gold, lithium, manganese, nickel, palladium, platinum, potassium, ruthenium, silver, sodium, sulphur, titanium, zinc, zirconium, vanadium and rare earth metals. Any of these elements can be either in elementary form or in ionic form.

The invention pertains to the use of the afore-described catalyst in Fischer-Tropsch processes. This generally refers to a process in which synthesis gas is converted into useful hydrocarbons.

Synthesis gas (or "syngas") generally refers to any gas feed stream comprising both hydrogen ($H_2$) and carbon monoxide (CO). Syngas can be obtained, e.g., by steam reforming of natural gas or liquid hydrocarbons to produce hydrogen, or the gasification of coal, of biomass, and in some types of waste-to-energy gasification facilities.

Essentially, syngas refers to a wide range of different amounts of carbon monoxide and hydrogen. Generally, the molar ratio of $H_2$:CO will range from 0.1 to 10. Preferred synthesis gas feeds for use in the invention have a molar ratio of $H_2$:CO below 3, and more preferably below 2. Most preferably, the molar ratio $H_2$:CO is within a range of from 0.5 to 1. In one preferred embodiment, a preferred source of syngas is coal. In another preferred embodiment, with a view to the preferred hydrogen to carbon monoxide ratios, the syngas feedstock used in the invention originates from biomass, and most preferably from non-food biomass, which will generally be lignocellulosic biomass.

The preference for ranges that are relatively low in hydrogen, is associated with the desire according to the invention to produce alkenes (which have a C:H ratio of 2, rather than alkanes (as in classical Fischer-Tropsch synthesis), that have a C:H ratio of [n]:[2n+2], with n being a positive integer.

In Fischer-Tropsch synthesis, and also in the case of Fischer-Tropsch steered to the formation of alkenes, generally a certain carbon chain-length distribution will result. The potential distribution of chain lengths is known to the skilled person as the Anderson-Schulz-Flory distribution which links selectivity to the probability of chain-growth. It is to be noted that also with catalysts that are highly selective in the formation of, e.g., one chain length, inevitably other chain lengths will be formed as well.

In the invention it will be clear that the Fischer-Tropsch synthesis is to be conducted so as to promote alkene formation. The invention specifically relates to the formation of lower olefins. The selectivity for lower olefins, particularly as this goes with an increased catalytic activity and undiminished catalyst stability, is an unexpected achievement.

Lower olefins generally are alkenes, and preferably 1-alkenes (α-olefins) having a chain length up to eight carbon atoms ($C_{2-8}$ olefins). E.g., highly useful products include $C_{5-8}$ α-olefins. Preferably, the invention pertains to olefins up to 6 carbon atoms ($C_{2-6}$ olefins). Most preferably, the invention pertains to the production of $C_{2-4}$ olefins, and even more preferably to the production of ethene and/or propene.

The skilled person will be generally aware how to steer a Fischer-Tropsch process towards the production of alkenes. Having the benefit of the selection of a catalyst according to the invention, the most important process parameters are temperature and pressure.

Particularly, in accordance with the invention, this preferably involves a reaction temperature above 270° C., preferably above 290° C., more preferably above 300° C., and most preferably above 310°. The reaction temperature preferably is not higher than 500° C., more preferably not higher than 450° C. and most preferably not higher than 400° C.

As to the reaction pressure, this is preferably 1-700 Bar, preferably 5-100 Bar, and most preferably 10-50 Bar.

In a particular preference, a temperature of 340-360° C. will be combined with a pressure of 15-25 Bar.

The Fischer-Tropsch synthesis of the invention can be carried out in any suitable reactor. Reactors to conduct Fischer-Tropsch processes are well-known to the skilled person, and do not require elucidation here. Similarly, the manner in which the catalyst is provided in the reactor is known. Preferably, a fluidized bed or a multitubular fixed-bed reactor is used. Further information can be found in FISCHER-TROPSCH TECHNOLOGY. A. Steynberg and M. Dry (Editors). Studies in Surface Science and Catalysis 152. Chapter 2: Fischer-Tropsch Reactors, Elsevier B.V. Amsterdam. 2004.

The invention further pertains to a novel process for the preparation of a catalyst as used in the invention. This process comprises the use of a technique to make iron-containing nanoparticles by the thermal decomposition of an organic iron complex. The feasibility of this technique has been established in the preparation of quantum dots and Ferro fluids, and the present inventors have now unexpectedly found its suitability for the preparation of supported iron catalysts. Reference is made to Guczi et al. Journal of Catalysis 244 (24-32), 2006. Herein iron oxide nanoparticles are prepared using iron oleate as a precursor. The purpose of this, however, is to provide carbon nanotubes with catalyst. To this end, after the particles are prepared and purified, they are redispersed in ethanol and deposited on multi-walled carbon nanotubes. In the process of the present invention, the thermal decomposition is particularly conducted in the presence of the support material.

Suitable iron complexes include, but are not limited to, iron oleate and iron salts from organic acids.

The invention will be illustrated hereinafter with reference to the following, non-limiting examples.

EXAMPLE 1

Catalyst Preparation. α-$Al_2O_3$ Supported Iron Catalyst (Ammonium Iron Citrate Precursor 13 wt % Fe)

Subsequent incipient wetness impregnation steps were performed at ambient pressure with 3.1 ml of a 1.8 M aqueous ammonium iron (III) citrate ($C_6H_{5+4y}Fe_xN_yO_7$, 15% wt Fe) solution on 2 g of α-$Al_2O_3$ spheres (sieve fraction: 212-425 m, BET surface area=10 m²/g, total pore volume=0.5 cm³/g) to provide 13 wt % Fe/α-$Al_2O_3$. After each impregnation the catalyst was dried at ambient temperature and 60 mbar for 2 hours. After all the solution was incorporated on the support, the sample was dried under air flow at 90° C. for 1 hour. Subsequently the sample was calcined under air flow at 500° C. for 2 hours.

Figure 1:
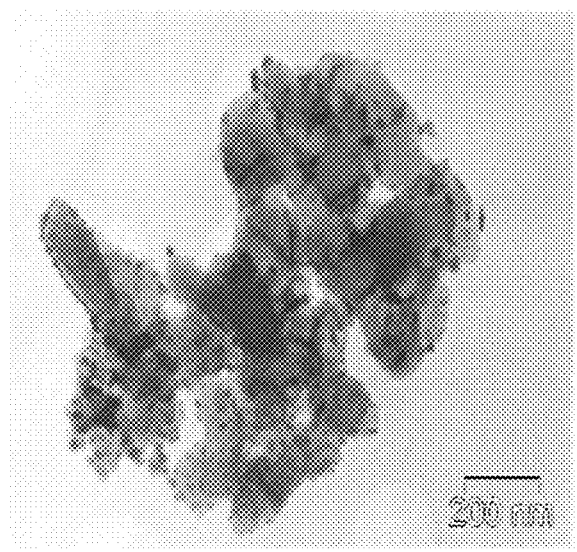
FIG. 1 is an electron micrograph of well-distributed $Fe_2O_3$ supported on α-alumina (in accordance with the invention; Sample A-1).

Characterization was performed by X-ray powder diffraction (XRD) and transmission electron microscopy (TEM). XRD patterns were obtained at room temperature from 30° to 85° 2θ with a Bruker-Nonius D8 Advance X-ray diffractometer set-up using Co—$K_{α12}$ (λ=1.79026 Å) radiation. The average iron oxide particle sizes were calculated according to the Scherrer equation, using the most intense diffraction line at 38.9°. The average crystallite size calculated from XRD was 21 nm and the average size calculated from TEM was 17 nm. TEM (FIG. 1) shows large —$Al_2O_3$ particles (approximately 200 nm) supporting iron oxide particles (approximately 17 nm) which are homogeneously distributed on the alumina surface. This sample was designated as sample A-1.

EXAMPLE 2

Catalyst Preparation. α-$Al_2O_3$ Supported Iron Catalyst (Ammonium Iron Citrate Precursor. Different Iron Loadings)

Subsequent incipient wetness impregnation steps were performed at ambient pressure with an aqueous ammonium iron (III) citrate ($C_6H_{5+4y}Fe_xN_yO_7$, 15% wt Fe) solution on 4 g of α-$Al_2O_3$ spheres (sieve fraction: 212-425 m, BET surface area=10 m²/g, total pore volume=0.5 cm³/g) to provide achieve four Fe/α-$Al_2O_3$ catalysts with different iron loadings. The samples were prepared following the preparation procedure from Example 1.

The amounts and composition of the ammonium iron citrate solutions and the resulting loadings are summarized in Table 1.

TABLE 1

Fe/—$Al_2O_3$ prepared using ammonium iron citrate as precursor

| Sample | Fe loading (% wt) | Ammonium iron citrate concentration (M) | mL of solution per 4 g of support |
|---|---|---|---|
| A-2 | 1 | 0.7 | 1.4 |
| A-3 | 2 | 1.5 | 1.3 |
| A-4 | 5 | 3.9 | 1.3 |
| A-5 | 20 | 24 | 1.3 |

The samples were designated as A-2 to A-5, as indicated in Table 1.

EXAMPLE 3

Catalyst Preparation. Mn Promoted and α-$Al_2O_3$ Supported Catalyst

Incipient wetness impregnation was performed at ambient pressure on 2 g of α-$Al_2O_3$ spheres (BET surface area=10 m²/g, total pore volume=0.5 cm³/g) with an aqueous solution of ammonium iron (III) citrate ($C_6H_{5+4y}Fe_xN_yO_7$, 15% wt Fe) and manganese (II) acetate ($Mn(CH_3COO)_2.4H_2O$). The solution was prepared by dissolving 0.24 g of the iron salt and 0.035 g or the manganese salt in 1 ml of demineralized water. After impregnation the catalyst was dried at 35° C. and 60 mbar for 2 hours. Subsequently the sample was calcined under air flow at 500° C. for 2 hours.

This sample was designated as sample A-6.

COMPARATIVE EXAMPLE 1

Catalyst Preparation. α-$Al_2O_3$ Supported Iron Catalyst (Iron Nitrate Precursor. Different Iron Loadings)

Subsequent incipient wetness impregnation steps were performed at ambient pressure with an aqueous iron (III) nitrate ($Fe(NO_3)_3.9H_2O$) solution on 4 g of α-$Al_2O_3$ spheres (sieve fraction: 212-425 m, BET surface area=10 m$^2$/g, total pore volume=0.5 cm$^3$/g) to provide achieve four Fe/α-Al$_2$O$_3$ catalysts with different iron loadings. After each impregnation the catalyst was dried at ambient temperature and 60 mbar for 2 hours. After all the solution was incorporated on the support, the sample was dried under air flow at 90° C. for 1 hour. Subsequently the sample was calcined under air flow at 500° C. for 2 hours.

The amounts and composition of the ammonium iron citrate solutions and the resulting loadings are summarized in Table 2.

TABLE 2

Fe/—Al$_2$O$_3$ prepared using iron nitrate as precursor

| Sample | Fe loading (% wt) | Iron nitrate concentration (M) | mL of solution per 4 g of support |
|---|---|---|---|
| C-1 | 1 | 0.8 | 0.9 |
| C-2 | 2 | 1.5 | 1.0 |
| C-3 | 5 | 3.4 | 1.1 |
| C-4 | 10 | 4 | 2 |

The samples were designated as C-1 to C-4, as indicated in Table 2.

Figure 2:
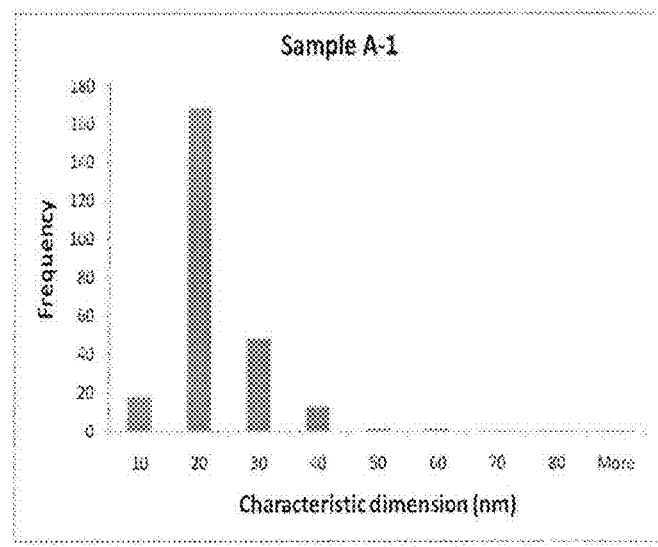
FIG. 2 is a bar diagram showing the relative numbers (frequency) of particle sizes of $Fe_2O_3$ supported on α-alumina (Sample A-1).

Characterization was performed by X-ray powder diffraction (XRD) and transmission electron microscopy (TEM). XRD patterns were obtained at room temperature from 30° to 85° 2θ with a Bruker-Nonius D8 Advance X-ray diffractometer set-up using Co—K$_{\alpha 12}$ (λ=1.79026 Å) radiation. The average iron oxide particle sizes were calculated according to the Scherrer equation, using the most intense diffraction line at 38.9°. The average crystallite size calculated from XRD was 21 nm and the average size calculated from TEM was 28 nm. TEM (FIG. 2) shows large —Al$_2$O$_3$ particles (approximately 200 nm) supporting iron oxide particles which agglomerate to form large Fe clusters (>30 nm).

COMPARATIVE EXAMPLE 2

Catalyst Preparation. Bulk Iron Catalyst 25 g of iron (III) nitrate (Fe(NO$_3$)$_3$.9H$_2$O were dissolved in 100 ml of demineralized water. The solution was heated to its boiling point after which it was slowly added, under vigorous stirring, a near boiling solution of 25 g of sodium carbonate (Na$_2$CO$_3$) in 100 ml of demineralized water. The resulting precipitate was filtered and re-slurried in 1 l of near boiling demineralized water to remove any residual sodium. The purification process was performed four times until neutral pH was reached. The purified precipitate was dried 6 hours at 60° C. and subsequently 24 hours at 120° C. under static air. The catalyst was calcined at 300° C. for 5 hours under air flow using a heating ramp of 5° C./min.

Characterization was performed by X-ray powder diffraction (XRD). XRD patterns were obtained at room temperature from 30° to 85° 2θ with a Bruker-Nonius D8 Advance X-ray diffractometer set-up using Co—K$_{12}$ (λ=1.79026 Å) radiation. The average iron oxide sizes were calculated according to the Scherrer equation, using the most intense diffraction line at 38.8°. The average crystallite size calculated from XRD was 27 nm. This sample was designated as sample C-5.

COMPARATIVE EXAMPLE 3

Catalyst Preparation. Promoted Bulk Iron Catalyst (Precipitation)

25 g of iron (III) nitrate (Fe(NO$_3$)$_3$.9H$_2$O and 1.2 g of copper (II) nitrate (Cu(NO$_3$)$_2$.3H$_2$O) were dissolved in 100 ml of demineralized water. The solution was heated to its boiling point after which a near boiling solution of 25 g of sodium carbonate (Na$_2$CO$_3$) in 100 ml of demineralized water was slowly under vigorous stirring. The resulting precipitate was filtered and re-slurried in 1 l of near boiling demineralized water to remove any residual sodium. The purification process was performed four times until neutral pH was reached. The purified precipitate was re-slurried in 200 ml of demineralized water and 8 g of potassium waterglass solution (K$_2$O:SiO$_2$ (1:2.15), Akzo-PQ) were added to the slurry under vigorous stirring. 1.5 ml of concentrated HNO$_3$ were added to precipitate the SiO$_2$ and to lower the total potassium content.

The obtained precipitate was dried 6 hours at 60° C. and subsequently 24 hours at 120° C. under static air. The catalyst was calcined at 300° C. for 5 hours under air flow using a heating ramp of 5° C./min.

Characterization was performed by X-ray powder diffraction and X-ray fluorescence (XRF). From XRF analysis it was determined that the catalyst contents 6% wt SiO$_2$ and 1.8% wt CuO and that potassium content was negligible. XRD patterns were obtained at room temperature from 30° to 85° 2θ with a Bruker-Nonius D8 Advance X-ray diffractometer set-up using Co—K$_{12}$ (λ=1.79026 Å) radiation. The average iron oxide sizes were calculated according to the Scherrer equation, using the most intense diffraction line at 38.9°. The average crystallite size calculated from XRD was 28 nm. This sample was designated as sample C-6.

COMPARATIVE EXAMPLE 4

Catalyst Preparation. Promoted Bulk Iron Catalyst (Sintering)

10 grams of catalyst were prepared by mixing 9.94 g of iron (II,III) oxide (Fe$_3$O$_4$), 3 g of titanium oxide (TiO$_2$), 0.72 g of zinc oxide (ZnO), and 0.42 g of potassium carbonate (K$_2$CO$_3$). The oxide mixture was sintered at 1050° C. for 4 hours.

Characterization was performed by X-ray powder diffraction (XRD). XRD patterns were obtained at room temperature from 30° to 85° 2θ with a Bruker-Nonius D8 Advance X-ray diffractometer set-up using Co—K$_{12}$ (λ=1.79026 Å) radiation. The average iron oxide sizes were calculated according to the Scherrer equation, using the most intense diffraction line at 38.8°. The average crystallite size calculated from XRD was 50 nm. This sample was designated as sample C-7.

COMPARATIVE EXAMPLE 5

Catalyst Preparation. Promoted and Heat Treated γ-Al$_2$O$_3$ Supported Iron Catalyst γ-Al$_2$O$_3$ (surface area ~250 m$^2$/g) was dried for 3 hours under static air at 200° C. After drying, the support was heated to 750° C. In a final step, temperature was raised to 1250° C. and the support remained at that temperature for 10 minutes. The obtained support is a mixture of alpha and gamma alumina as confirmed by XRD analysis. 4 g of HT (heat treated) γ-Al$_2$O$_3$ were impregnated with 2.6 ml of a praseodymium nitrate solution prepared as follows: 3.1 g of praseodymium (III,IV) oxide (Pr$_6$O$_{11}$) were dissolved in 2.5 ml of concentrated HNO$_3$. The solution was heated until water was evaporated and the remaining solid was dried overnight under static air at 100° C. The obtained praseodymium nitrate was dissolved in water and made up to 25 ml. After impregnation, the sample was dried 20 h under vacuum and afterwards it was dried 1 hour at 90° C. under air flow. The impregnated support was calcined under air flow at 500° C. for 1.5 hours.

Figure 3:
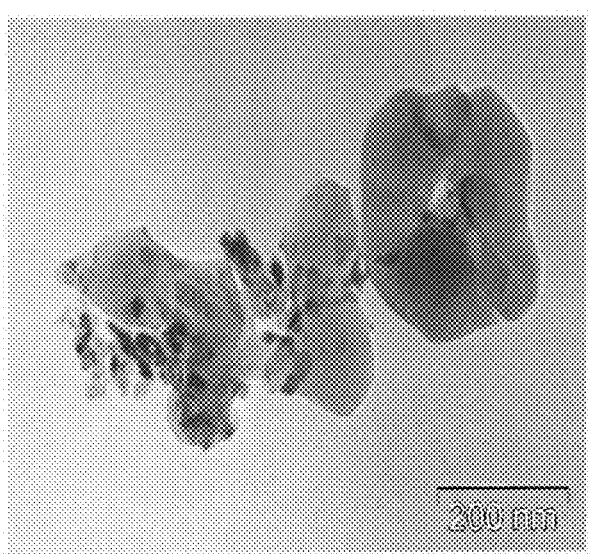
FIG. 3 is an electron micrograph of clustered $Fe_2O_3$ supported on α-alumina (not in accordance with the invention; Sample C-4).
Figure 4:
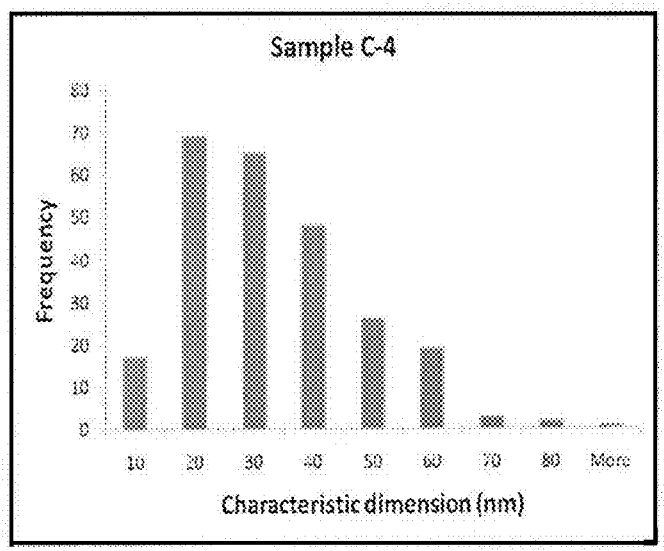
FIG. 4 is a bar diagram showing the relative numbers (frequency) of particle sizes of $Fe_2O_3$ supported on α-alumina (Sample C-4).

After the first calcination, the sample was impregnated with an iron (III) nitrate ($Fe(NO_3)_3 \cdot 9H_2O$) solution prepared by dissolving 0.286 g of the iron salt in 1.3 ml of demineralized water. Subsequently the sample was dried for 20 hours under vacuum followed by a drying step at 90° C. for 1 h. A final calcination step was performed under air flow at 450° C. for 2 hours. TEM indicates that the surface of the α-alumina phase of the support (150-200 nm —$Al_2O_3$ crystals) is mainly free of $Fe_2O_3$ particles (FIG. 3). This sample was designated as sample C-8.

COMPARATIVE EXAMPLE 6

Catalyst Preparation. γ-$Al_2O_3$ Supported Iron Catalyst

Subsequent incipient wetness impregnation steps were performed at ambient pressure with 3.1 ml of a 1.8 M aqueous ammonium iron (III) citrate ($C_6H_{5+4y}Fe_xN_yO_7$, 15% wt Fe) solution on 2 g of γ-$Al_2O_3$ spheres (BET surface area=250 m²/g) to provide 13 wt % Fe/γ-$Al_2O_3$. The sample was prepared following the preparation procedure from Example 1. This sample was designated as sample C-9.

EXAMPLE 4

Catalytic Tests at Low Pressure ($H_2$/CO=1)

For the catalytic tests, 20 mg of any of the catalysts described in Examples 1 to 6 and Comparative Examples 1 to 3 were mixed with 200 mg of SiC as catalyst bed dilutant. The sample to be tested was placed in a plug flow reactor (diameter 5 mm) and reduced under a mixture of hydrogen (33% v/v) and argon (67% v/v) with a gas hourly space velocity of 42000 $h^{-1}$ at 1 bar and 350° C. for 2 h (5° C./min) After reduction the feed was switched to a mixture with 50%v/v hydrogen and 50%v/v carbon monoxide (GHSV=4200 h-¹). The Fischer-Tropsch reaction was carried out at 1 bar and 350° C. for 20 hours.

The results of the catalytic tests after 15 hours of reaction are summarized in Table 3 below. From these results it can be observed that samples A-1, A-4 and A-6 show low methane selectivity (≤22%) and high selectivity to lower olefins (≥58%) at low pressures (1 bar). The samples from the comparative examples C-3 and C-5 to C-9 show high methane selectivity (≥43%) and a moderate selectivity towards light olefins (≤46%). Sample A-4 shows the highest catalytic activity.

TABLE 3

Catalytic tests at 1 bar, 350° C., $H_2$/CO = 1 (TOS = 15 h)

| | Product selectivity* | | | |
|---|---|---|---|---|
| Sample | $CH_4$ (wt %) | $C_2$-$C_4$ olefins (wt %) | $C_5^+$ (wt %) | Activity ($mol_{CO}/g_{Cat} \cdot s$) |
| A-1 | 22 | 61 | 13 | $7.7 \times 10^{-8}$ |
| A-4 | 17 | 63 | 18 | $3.4 \times 10^{-7}$ |
| A-6 | 18 | 58 | 16 | $5.8 \times 10^{-8}$ |
| C-3 | 73 | 22 | 2 | $7.9 \times 10^{-8}$ |
| C-5 | 76 | 21 | 1 | $4.8 \times 10^{-8}$ |
| C-6 | 43 | 46 | 9 | $6.4 \times 10^{-8}$ |
| C-7 | 83 | 16 | 0 | $9.0 \times 10^{-8}$ |
| C-8 | 50 | 37 | 5 | $7.6 \times 10^{-8}$ |
| C-9 | 54 | 44 | 0 | $1.2 \times 10^{-8}$ |

*Hydrocarbons only

EXAMPLE 5

Catalytic Tests at Medium Pressure ($H_2$/CO=1)

For the catalytic tests, 2 ml of any of the catalysts described in Examples 1 and 2 were mixed with 10 ml of SiC as catalyst bed dilutant. The sample to be tested was placed in a plug flow reactor (diameter 7 mm) and reduced under a mixture of hydrogen and argon with a gas hourly space velocity of 660 $h^{-1}$ at 2.5 bar and 350° C. for 2 h.

After reduction the temperature was decreased to 280° C. and the feed was switched to a mixture of hydrogen (50% v/v) and carbon monoxide (50% v/v) with a gas hourly space velocity of 1500 $h^{-1}$. After the introduction of synthesis gas (P=20 bar), reaction temperature was increased to 340° C. with a ramp of 100° C./h. After 6 hours the temperature was decreased to 280° for 33 hours after which temperature was increased to 340° C. to resume the measurements at high temperature. During the experiments performed at 20 bar, the concentrations of CO, $CO_2$ and hydrocarbons from $C_1$-$C_{10}$ in the outlet were measured with a GC. Small amounts of liquid products formed during reaction were ignored in the data analysis.

The results of the catalytic tests after 65 hours of reaction are summarized in Table 4.

TABLE 4

Catalytic tests at 20 bar, 340° C., $H_2$/CO = 1 (TOS = 65 h)

| | Product selectivity* | | | |
|---|---|---|---|---|
| Sample | $CH_4$ (wt %) | $C_2$-$C_4$ olefins (wt %) | $C_5^+$ (wt %) | Activity ($mol_{CO}/g_{Cat} \cdot s$) |
| A-1 | 17 | 39 | 14 | $3.2 \times 10^{-6}$ |
| A-2 | 24 | 55 | 5 | $3.4 \times 10^{-7}$ |
| A-3 | 21 | 53 | 11 | $4.3 \times 10^{-7}$ |
| A-4 | 24 | 35 | 10 | $4.8 \times 10^{-6}$ |
| A-5 | 11 | 53 | 21 | $3.4 \times 10^{-6}$ |
| A-6 | 24 | 38 | 19 | $6.1 \times 10^{-7}$ |
| C-1 | 28 | 32 | 13 | $3.3 \times 10^{-6}$ |
| C-2 | 36 | 27 | 8 | $3.8 \times 10^{-6}$ |
| C-3 | 39 | 20 | 7 | $5.6 \times 10^{-6}$ |
| C-4 | 38 | 16 | 6 | $5.8 \times 10^{-6}$ |
| C-5 | 30 | 32 | 14 | $3.6 \times 10^{-6}$ |
| C-6 | 26 | 36 | 19 | $3.6 \times 10^{-6}$ |
| C-7 | 24 | 28 | 10 | $3.6 \times 10^{-6}$ |
| C-8 | 42 | 23 | 8 | $8.6 \times 10^{-7}$ |
| C-9 | 49 | 33 | 1 | $3.2 \times 10^{-7}$ |

*Hydrocarbons only

From these results it can be observed that the samples A-1 to A-6 showed low selectivity to methane (≤24%) and high selectivity towards $C_2$-$C_4$ olefins (≥38%) when the high temperature Fischer-Tropsch reaction is carried out at high pressure (20 bar).

The invention claimed is:

1. A process for the preparation of an iron-based supported catalyst composition comprising an iron component dispersed onto a support comprising α-alumina, the process comprising decomposing an organic iron complex under the influence of heat to form iron oxide nanoparticles, wherein decomposing the organic iron complex is conducted in the presence of the support material.

2. A process according to claim 1, wherein the iron component comprises iron-containing particles having an average particle size smaller than 30 nm.

3. A process according to claim 2, wherein the iron-containing particles are obtainable from a precursor selected from the group consisting of iron acetates, iron fumarates, iron gluconates, iron citrates, iron benzoates, iron maleates, iron oxalates, iron oleates, and iron stearates.

4. A process according to claim 2, wherein said particle size is smaller than 20 nm.

5. A process according to claim 3, wherein the iron-containing particles are iron oxide particles.

6. A process according to claim 3, wherein the precursor is ammonium iron (III) citrate.

\* \* \* \* \*